United States Patent [19]

Seitz et al.

[11] Patent Number: 5,723,646

[45] Date of Patent: Mar. 3, 1998

[54] SUBSTITUTED AMINO ACID AMIDE DERIVATIVES THEIR PREPARATION AND USE AS FUNGICIDES

[75] Inventors: Thomas Seitz; Heinz-Wilhelm Dehne, both of Monheim, Germany

[73] Assignee: Bayer Aktiengesellschaft, Leverkusen, Germany

[21] Appl. No.: 821,674

[22] Filed: Jan. 16, 1992

[30] Foreign Application Priority Data

Jan. 24, 1991 [DE] Germany ............... 41 02 042.1

[51] Int. Cl.$^6$ .................................................. C07C 261/00
[52] U.S. Cl. .................. 560/27; 546/265; 546/283; 546/284; 546/286; 546/291; 549/59; 549/61; 549/76; 549/448; 549/452; 558/417; 560/13; 560/22
[58] Field of Search ............... 560/27, 13, 22; 558/417; 546/265, 283, 284, 286, 291; 549/59, 61, 76, 448, 452

[56] References Cited

U.S. PATENT DOCUMENTS

| | | | |
|---|---|---|---|
| 2,576,106 | 11/1951 | Cusik | 564/192 |
| 2,768,154 | 10/1956 | Unruh et al. | 560/24 |
| 3,321,464 | 5/1967 | Soboczenski | 560/115 |
| 3,393,224 | 7/1968 | Brookes et al. | 560/24 |
| 3,808,191 | 4/1974 | Poduska et al. | |
| 3,919,313 | 11/1975 | Villani | 564/193 |
| 4,021,224 | 5/1977 | Pallos et al. | 560/159 |
| 4,138,422 | 2/1979 | Chan et al. | 560/24 |
| 4,259,234 | 3/1981 | Smithwick, Jr. et al. | 930/20 |
| 4,277,473 | 7/1981 | Inamoto | 564/193 |
| 4,322,342 | 3/1982 | Smithwick, Jr. et al. | 930/20 |
| 4,325,966 | 4/1982 | Punga | 560/24 |
| 4,501,756 | 2/1985 | Kato et al. | 560/24 |
| 4,610,985 | 9/1986 | Führer et al. | 560/24 |
| 4,639,468 | 1/1987 | Roncucci et al. | 560/159 |
| 4,666,938 | 5/1987 | Takahashi et al. | 560/24 |
| 4,804,782 | 2/1989 | Brennan | 564/193 |
| 4,818,748 | 4/1989 | Bender et al. | 514/17 |
| 4,939,170 | 7/1990 | Krüger et al. | 560/9 |
| 4,996,358 | 2/1991 | Handa et al. | 562/622 |
| 5,158,962 | 10/1992 | Seitz | 514/335 |

FOREIGN PATENT DOCUMENTS

| | | | |
|---|---|---|---|
| 0046707 | 3/1982 | European Pat. Off. | |
| 247557 | 12/1987 | European Pat. Off. | |
| 343460 | 11/1989 | European Pat. Off. | |
| 0374952 | 6/1990 | European Pat. Off. | |
| 0493683 | 11/1991 | European Pat. Off. | |
| 47-27011 | 7/1972 | Japan | 514/488 |
| 49-16933 | 4/1974 | Japan | 514/488 |
| 49-31094 | 8/1974 | Japan | 514/488 |
| 0873049 | 7/1961 | United Kingdom. | |

OTHER PUBLICATIONS

Chemical Abstracts, vol. 102, No. 13, p. 761 (Apr. 1, 1985), :102:113961g, Gesellchen et al.

Chemical Abstracts, vol. 110, No. 15 (Apr. 10, 1989), 110: 135676k Breslav et al.

Chemical Abstracts, vol. 109, No. 11, p. 773 (Sep 1988), 109:93603F, Tsuchiya et al.

Thaisrivongs et al, "Design and Synthesis of Potent and Specific Renin . . . ", J.Med.Chem. V. 29, (1986), pp. 2080–2087.

Bulletin of the Chemical Society of Japan, Sep., 1967, by Shumpei Sakakibara, pp. 2164–2167.

Corwin Hansch, *Journal of Medicinal Chemistry*, Dec. 26, 1967, pp. 5, and 74–79.

*Primary Examiner*—Michael L. Shippen
*Attorney, Agent, or Firm*—Sprung Kramer Schaefer & Briscoe

[57] ABSTRACT

There are described new amino acid amide derivatives, some of which are known, of the formula (I)

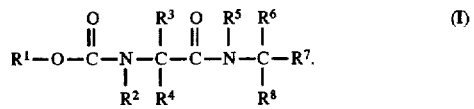

in which $R^1$ to $R^8$ have the meaning given in the description, and a process for their preparation. The amino acid amide derivatives of the formula (I) are used for the preparation of pesticides.

1 Claim, No Drawings

SUBSTITUTED AMINO ACID AMIDE DERIVATIVES THEIR PREPARATION AND USE AS FUNGICIDES

The present invention relates to new substituted amine acid amide derivatives, to a process for their preparation, and to their use in pesticides.

The substances according to the invention have an outstanding action when used for combating pests. The substances according to the invention can be used, in particular, as fungicides, especially in plant protection.

Certain amino acid amides have already been disclosed, such as, for example, N-tert-butoxycarbonyl-L-leucyl-benzylamide (EP-A-236,874).

However, the use of these compounds in pesticides has not been described.

Furthermore, there have been disclosed certain substituted amino acid amide derivatives such as, for example, N-(t-butyloxycarbonyl)-L-valine-phenylethylamide (DE-OS (German Published Specification) 3,915,755). However, the action of these compounds is not satisfactory, in particular when low amounts and concentrations are applied.

Moreover, it has been disclosed that certain diphenylmethyl amino acid amide derivatives such as, for example, [1-[[(diphenylmethyl)-amino]carbonyl]-2-methylpropyl]-1,1-dimethylethyl carbamate have pharmacological activity (cf. EP-OS (European Published Specification) 343,460, EP-OS (European Published Specification) 247,557).

The invention relates to new substituted amino acid amide derivatives of the general formula (I)

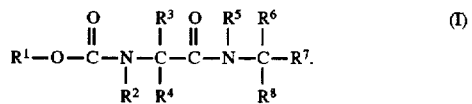

In this formula, $R^1$ 1. represents alkyl, alkenyl, alkinyl, halogenoalkyl, halogenoalkenyl, halogenoalkinyl, cycloalkyl, cycloalkenyl, unsubstituted or substituted aryl and unsubstituted or substituted heteroaryl,
2. preferably represents straight-chain or branched alkyl having 1 to 6 carbon atoms, straight-chain or branched alkenyl or alkinyl having 2 to 6 carbon atoms, straight-chain or branched halogenoalkyl having 1 to 6 carbon atoms and 1 to 9 identical or different halogen atoms, straight-chain or branched halogenoalkenyl or halogenoalkinyl having 2 to 6 carbon atoms and 1 to 9 identical or different halogen atoms, or represents substituted or unsubstituted cycloalkyl or cycloalkenyl having 3 to 7 carbon atoms, or represents phenyl or pyridyl, each of which is unsubstituted or substituted, suitable substituents in the pyridyl or phenyl moiety in each case being: alkyl, alkoxy and alkylthio, each of which has 1 to 4 carbon atoms; halogenoalkyl, halogenoalkoxy and halogenoalkylthio, each of which has 1 to 4 carbon atoms and 1 to 9 halogen atoms, the halogen atoms being identical or different; halogen; alkylalkoxy having 1 to 4 carbon atoms in each alkyl moiety; carbonylalkoxy having 1 to 4 carbon atoms in the alkyl moiety;
3. particularly preferably represents straight-chain or branched alkyl having 1 to 4 carbon atoms, straight-chain or branched alkenyl or alkinyl having 2 to 4 carbon atoms, straight-chain or branched halogenoalkyl having 1 to 4 carbon atoms and 1 to 5 identical or different halogen atoms, straight-chain or branched halogenoalkenyl or halogenoalkinyl having 2 to 4 carbon atoms and 1 to 5 identical or different halogen atoms, or represents unsubstituted or substituted cycloalkyl or cycloalkenyl having 3 to 6 carbon atoms, or represents phenyl which is unsubstituted or monosubstituted to trisubstituted by identical or different substituents, suitable substituents being the following: alkyl, alkoxy and alkylthio, each of which has 1 to 4 carbon atoms; halogenoalkyl, halogenoalkoxy and halogenoalkylthio, each of which has 1 or 2 carbon atoms and 1 to 5 halogen atoms, the halogen atoms being identical or different; fluorine, chlorine, bromine and iodine; alkylalkoxy having 1 to 2 carbon atoms in each alkyl moiety; carbonylalkoxy having 1 or 2 carbon atoms in the alkyl moiety;
4. very particularly preferably represents methyl, ethyl, n- and i-propyl, n-, i-, s- and t-butyl, fluoromethyl, fluoroethyl, fluoropropyl, chloropropyl, fluorobutyl, chlorobutyl, difluoromethyl, difluoropropyl, dichloropropyl, difluorobutyl, dichlorobutyl, trifluoromethyl, trichloromethyl, trifluoroethyl, trichloroethyl, trifluoropropyl, trichloropropyl, trifluorobutyl, trichlorobutyl, allyl, butenyl, propargyl, butinyl, fluoro- or chloroallyl, -butenyl, -propargyl, -butinyl, cyclopropyl, cyclopentyl, cyclohexyl, cyclopentenyl or cyclohexenyl, or represents phenyl which is unsubstituted or monosubstituted to disubstituted by identical or different substituents, suitable substituents being the following: methyl, ethyl, n- and i-propyl, n-, i-, s- and t-butyl, methoxy, ethoxy, i- and n-propoxy, n-, i-, s- and t-butoxy, trifluoromethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy and trifluoromethylthio; chlorine, bromine, fluorine.

$R^2$ and $R^5$ independently of one another
1. represent hydrogen or alkyl;
2. preferably represent hydrogen or methyl;
3. particularly preferably represent hydrogen.

$R^3$ and $R^4$ independently of one another
1. represent hydrogen, cycloalkyl or alkyl, or together with the carbon atom to which they are bonded form a cycloalkyl ring;
2. preferably represent hydrogen, unsubstituted or substituted cycloalkyl having 3 to 7 carbon atoms or straight-chain or branched alkyl having 1 to 6 carbon atoms, or together with the carbon atom to which they are bonded form a cycloalkyl ring having 3 to 7 carbon atoms;
3. particularly preferably represent hydrogen unsubstituted or substituted cycloalkyl having 3 to 6 carbon atoms or straight-chain or branched alkyl having 1 to 5 carbon atoms, or together with the carbon atom to which they are bonded form a cycloalkyl ring having 3 to 6 carbon atoms;
4. very particularly preferably represent hydrogen, methyl, ethyl, n- or i-propyl, n-, i-, s- or t-butyl, 3-pentyl, cyclopropyl, cyclopentyl or cyclohexyl, or together with the carbon atom to which they are bonded form a cyclopropyl, cyclopentyl or cyclohexyl ring.

$R^6$
1. represents hydrogen or alkyl,
2. preferably represents hydrogen or branched or unbranched alkyl having 1 to 6 carbon atoms,
3. particularly preferably represents hydrogen or branched or unbranched alkyl having 1 to 4 carbon atoms, 4. very particularly preferably represents hydrogen, methyl, ethyl or n- and iso-propyl.

R$^7$ and R$^8$ independently of one another 1. represent phenyl or heteroaryl, each of which is unsubstituted or substituted,
2. preferably represent in each case unsubstituted or substituted phenyl, pyridyl, furanyl or thienyl, suitable substituents in each case being: alkyl, alkoxy and alkylthio, each of which has 1 to 4 carbon atoms; halogenoalkyl, halogenoalkoxy and halogenoalkylthio, each of which has 1 to 4 carbon atoms and 1 to 9 halogen atoms, the halogen atoms being identical or different; hydroxyl; halogen; cyano; nitro; dialkylamino having 1 to 4 carbon atoms per alkyl group; carboxyl; alkylalkoxy having 1 to 4 carbon atoms in each alkyl moiety; carbonylalkoxy having 1 to 4 carbon atoms in the alkyl moiety; carbonylalkyl having 1 to 4 carbon atoms in the alkyl moiety; formyl; carbonylaryloxy having 6 to 10 carbon atoms in the aryl moiety; carbonylaryl having 6 to 10 carbon atoms in the aryl moiety; oxycarbonylalkyl having 1 to 4 carbon atoms in the alkyl moiety; oxycarbonylaryl having 6 to 10 carbon atoms in the aryl moiety; carbonylamino, carbonylaminoalkyl, carbonylaminodialkyl, aminocarbonyl, alkylaminocarbonyl, aminocarbonylalkyl and alkylaminocarbonylalkyl, each of which has 1 to 4 carbon atoms in the alkyl moiety; sulphonamido; sulphonylalkyl and sulphonylalkoxy, each of which has 1 to 4 carbon atoms; phenyl or phenoxy, each of which is unsubstituted or substituted by halogen;
3. particularly preferably represent phenyl, pyridyl, thienyl or furanyl, each of which is unsubstituted or substituted, suitable substituents being: alkyl, alkoxy and alkylthio, each of which has 1 or 2 carbon atoms; halogenoalkyl, halogenoalkoxy and halogenoalkylthio having 1 or 2 carbon atoms and 1 to 5 halogen atoms, the halogen atoms being identical or different; hydroxyl; fluorine, chlorine, bromine and iodine; cyano; nitro; dialkylamino having 1 or 2 carbon atoms per alkyl group; carboxyl; alkylalkoxy having 1 or 2 carbon atoms in each alkyl moiety; carbonylalkoxy having 1 or 2 carbon atoms in the alkyl moiety; carbonylalkyl having 1 or 2 carbon atoms in the alkyl moiety; formyl; carbonylphenoxy; benzoyl; oxycarbonylalkyl having 1 or 2 carbon atoms; benzoyloxy; carbonylamino, carbonylaminoalkyl, carbonylaminodialkyl, aminocarbonyl, alkylaminocarbonyl, aminocarbonylalkyl and alkylaminocarbonylalkyl, each of which has 1 or 2 carbon atoms in the alkyl moiety; sulphonamido; sulphonylalkyl and sulphonylalkoxy, each of which has 1 or 2 carbon atoms; phenyl or phenoxy, each of which is unsubstituted or substituted by fluorine, chlorine or bromine.
4. very particularly preferably represent phenyl, pyridyl, furanyl or thienyl, each of which is unsubstituted or substituted, suitable phenyl substitutents being methyl, ethyl, n- and i-propyl, n-, i-, s- and t-butyl, methoxy, ethoxy, i- and n-propoxy, n-, i-, s- and t-butoxy, trifluoromethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy and trifluoromethylthio; chlorine, bromine, fluorine, nitro and cyano, and suitable heteroaryl substituents being chlorine, fluorine, bromine and methyl.

The compound [1-[[(diphenylmethyl)-amino]-carbonyl]-2-methylpropyl]-1,1-dimethylethyl carbamate is excepted.

The definitions of the individual radicals mentioned here also apply analogously to all combinations of the radicals in the compound of the formula (I) and to the intermediates and precursors.

In this context, the radicals R$^1$ to R$^8$ are combined in any desired manner within the scope of their general and preferred definitions given in each case (see preferred ranges 1. to 4.).

Combinations of the radicals R$^1$ to R$^8$ which are of particular interest are those from the same preferred ranges in each case, but in particular the combination of the radicals R$^1$, R$^3$, R$^4$, R$^6$, R$^7$ and R$^8$ in the preferred range 4. with the radicals R$^2$ and R$^5$ in the preferred range 3.

Especially preferred are the substituted amino acid amide derivatives of the general formula (I) in which R$^1$, R$^2$, R$^5$, R$^6$, R$^7$ and R$^8$ have the meanings given above, in particular those in the preferred ranges, and R$^3$ represents methyl, ethyl, n-propyl, t-butyl, i-butyl, 3-pentyl, cyclopentyl or cyclohexyl in particular i-propyl, s-butyl or cyclopentyl, R$^4$ represents hydrogen or R$^3$ and R$^4$ together with the carbon atom to which they are bonded form a cycloalkyl ring having 3 to 6 carbon atoms, in particular a cyclopropyl, cyclopentyl or cyclohexyl ring.

with the exception of the compound [1-[[(diphenylmethyl)amino]-carbonyl]-2-methylpropyl]-1,1-dimethylethyl carbamate.

Some of the substituted amino acid amide derivatives of the formula (I) to be used according to the invention are known (cf. EP-OS (European Published Specification) 343, 460 and EP-OS (European Published Specification) 247, 557). However, the use of these compounds in pesticides has not been described.

The present application therefore also relates to the use of the above-described new compounds of the formula (I) and the known compound [1-[[(diphenylmethyl)-amino]carbonyl]-2-methylpropyl]-1,1-dimethylethyl carbamate as fungicides.

Surprisingly, the substituted amino acid amide derivatives of the formula (I) to be used according to the invention show a more powerful fungicidal activity than N-(t-butyloxycarbonyl)-L-valine-phenyl-ethylamide, which is known from the prior art.

The substituted amino acid amide derivatives of the general formula (I)

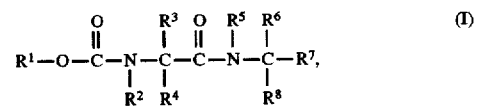

in which

R$^1$, R$^2$, R$^3$, R$^4$, R$^5$, R$^6$, R$^7$ and R$^8$ have the abovementioned meaning, are obtained when substituted amino acid of the formula (II)

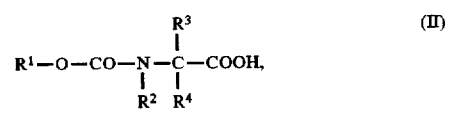

in which

R$^1$, R$^2$, R$^3$ and R$^4$ have the abovementioned meaning, or their carboxyl-activated derivatives, are reacted with an amine of the formula (III)

in which

R[5], R[6], R[7] and R[8] have the abovementioned meaning, if appropriate in the presence of a catalyst, if appropriate in the presence of an acid-binding agent and if appropriate in the presence of a diluent.

The known compounds can be obtained analogously to the process for the preparation of the compounds of the formula (I).

Moreover, the known compounds and the compounds of the formula (I) can contain one or more chiral centres and can therefore be in the form of various mixtures of enantiomers and diastereomers, all of which can, if desired, be separated in the customary fashion. The invention claims the pure enantiomers and diastereomers as well as the mixtures.

For simplicity's sake, the following text will always refer to compounds of the formula (I), even though this is understood as meaning the pure compounds as well as the mixtures with various proportions of isomeric, enantiomeric and diastereomeric compounds.

If, for example, i-propoxycarbonyl-L-valine and α-aminodiphenylmethane are used as starting substances, the course of the process according to the invention can be described by the following equation:

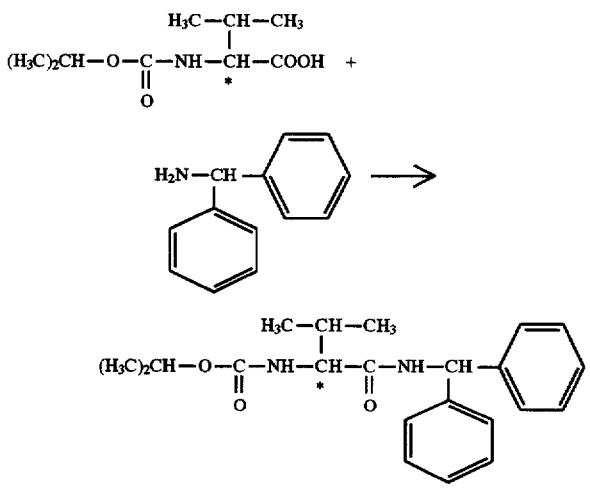

The amino acid derviatives of the formula (II) are generally known (cf., for example, Houben-Weyl, Methoden der organischen Chemie, [Methods in Organic Chemistry], Vol. XV, part 1 and 2, pages 46 et seq. and 112 et seq., Georg Thieme Verlag, Stuttgart 1974; D. Keller et. al., Org. Synth. 60, 2145 (1981); or R. C. Sheppard, A Specialist Periodical Report, Amino-acids, Peptids and Proteins, The Royal Society of Chemistry, Burlington House, London 1978, or I. P. Greenstein and M. Winitz, Chemistry of Amino Acids, I. Wiley Sons Inc., New York, London 1961; bzw. E. Schröder and K. Lübke, The Peptides Vol. I, Academic Press, New York, London 1965), or they can be obtained by the processes mentioned therein.

The carboxyl-activated derivatives of the amino acid of the formula (II) which are furthermore to be used as starting substances for carrying out the process according to the invention are generally known.

Suitable carboxyl-activated derivatives of the amino acids of the formula (II) are all carboxyl-activated derivatives such as acid halides such as, for example, acid chlorides, acid azides, furthermore symmetrical and mixed anhydrides such as, for example, the mixed O-alkyl carbonic anhydrides, furthermore activated esters such as, for example, p-nitrophenyl esters or n-hydroxy-succinimide esters, as well as activated forms of the amino acids which have been prepared in situ by means of condensing agents such as, for example, dicyclohexylcarbodiimide or carbonyldiimidazole.

It is preferred to employ the acid chlorides and mixed anhydrides which correspond to the amino acids of the formula (II). They can be prepared by reacting the amino acids of the formula (II) or their salts with a halogenating agent or with one of the generally known agents for preparing mixed anhydrides, such as, for example, phosphorus pentachloride, thionyl chloride oxalyl chloride or isobutyl chloroformate, in a generally known fashion. It is preferred to employ isobutyl chloroformate.

This reaction can be carried out in the presence of indifferent diluents such as, for example, aromatic, nonaromatic or halogenated hydrocarbons such as: ketones such as, for example, acetone; esters such as, for example, ethyl acetate; amides such as, for example, dimethylformamide-; nitriles such as, for example, acetonitriles; chlorohydrocarbons such as, for example, methylene chloride; hydrocarbons such as, for example, toluene; or ethers such as, for example, tetrahydrofuran, or their mixtures, and/or in the presence of an acid-binding agent such as, preferably, a tertiary amine such as, for example, triethylamine, pyridine or N-methylpiperidine, at temperatures from −78° C. to 100° C., preferably −60° C. to 25° C.

The amines of the formula (III) are generally known compounds of organic chemistry.

Suitable diluents in the process according to the invention are inert organic solvents such as: ketones such as acetone or ethyl methyl ketone; esters such as ethyl acetate or methyl acetate; amides such as dimethylformamide; nitriles such as acetonitrile; chlorohydrocarbons such as methylene chloride or carbon tetrachloride; hydrocarbons such as toluene, or ethers such as tetrahydrofuran and, if appropriate, water and their mixtures.

Suitable acid-binding agents in the process according to the invention are customary inorganic and organic acid binders. These preferably include tertiary amines such as triethylamine, pyridine or N-methylpyridine, and inorganic bases, for example metal hydroxides such as sodium hydroxide and potassium hydroxide, or metal carbonates such as sodium carbonate or calcium carbonate.

If appropriate, the process according to the invention is carried out in the presence of a catalyst. Examples which may be mentioned are 4-dimethylaminopyridine, 1-hydroxy-benzotriazole or dimethylformamide.

When carrying out the process, the temperatures can be varied within a substantial range. In general, the process is carried out at temperatures from −78° to +120° C., preferably at −60° to +40° C.

The process according to the invention is preferably carried out using equimolar amounts.

For this purpose, the amino acid derivatives of the formula (II) are employed in the form of pure optical isomers (D or L form) or in the form of racemates.

The invention embraces the pure isomers as well as the mixtures. These mixtures can be separated into the components using customary methods, for example selective crystallisation from suitable solvents, or chromatography on silica gel or aluminium oxide. Racemates can be resolved to give the individual enantiomers by customary methods, for example by salt formation with optically active acids such as champhorsulfonic acid or dibenzoyl tartaric acid, and selective crystallisation, or by the formation of derivatives with suitable optically active reagents, separation of the diastereomeric derivatives, and back conversion or separation on optically active column material.

The known active compounds of the formula (I) and the active compounds of the formula (I) according to the invention exhibit a powerful action against pests and can be employed in practice for combating undesired harmful organisms. The active compounds are suitable for use as plant protection agents, in particular as fungicides.

Fungicidal agents in plant protection are employed for combating Plasmodiophoromycetes, Oomycetes, Chytridiomyceres, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum*;
Phytophthora species, such as, for example, *Phytophthora infestans*;
Pseudoperonospora species, such as, for example, *Pseudoperonospora humuli* or *Pseudoperonospora cubensis*;
Plasmopara species, such as, for example, *Plasmopara viticola*;
Peronospora species, such as, for example, *Peronospora pisi* or *P. brassicae*;
Erysiphe species, such as, for example, *Erysiphe graminis*;
Sphaerotheca species, such as, for example, *Sphaerotheca fuliginea*;
Podosphaera species, such as, for example, *Podosphaera leucotricha*;
Venturia species, such as, for example, *Venturia inaequalis*;
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus*; Puccinia species, such as, for example, *Puccinia recondita*;
Tilletia species, such as, for example *Tilletia caries*;
Ustilago species, such as, for example, *Ustilago nuda* or *Ustilago avenae*;
Pellicularia species, such as, for example, *Pellicularia sasakii*;
Pyricularia species, such as, for example, *Pyricularia oryzae*;
Fusarium species, such as, for example, *Fusarium culmorum*;
Botrytis species, such as, for example, *Botrytis cinerea*;
Septoria species, such as, for example, *Septoria nodorum*;
Leptosphaeria species, such as, for example, *Leptosphaeria nodorum*;
Cercospora species, such as, for example, *Cercospora canescens*;
Alternaria species, such as, for example, *Alternaria brassicae* and
Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success protectively for combating Phytophthora species on tomatoes or Plasmopara species on grapevines.

Depending on their particular physical and/or chemical properties, the active compounds can preferably be converted into customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipid, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs, and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilisers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomising, scattering, dusting, foaming, brushing on and the like. It is furthermore possible to apply the active compounds by the ultra-low volume method or to inject the active compound formulation or the active compound itself into the soil. The seeds of plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The preparation and the use of the active compounds according to the invention will be illustrated by the examples which follow.

PREPARATION EXAMPLES

Example 1

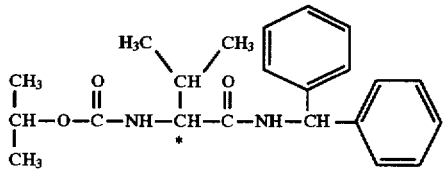

To 4.67 g of i-propoxycarbonyl-L-valine (0.023 mol), dissolved in 50 ml of $CH_2Cl_2$, there were added at $-20°$ C. 2.3 g (0.023 mol) of N-methylpiperidine. 3.2 g (0.023 mol) of isobutyl chloroformate are subsequently rapidly added dropwise at $-20°$ C., stirring is continued at the same temperature for 10 minutes, the mixture is cooled to $-60°$ C., and 4.21 g (0.023 mol) of α-aminodiphenylmethane, dissolved in 10 ml of dichloromethane, are run in, during which process the temperature is kept below $-15°$ C.

After 2 hours at $-15°$ C., stirring is continued for 15 hours at room temperature, the solid substance is filtered off and washed with $CH_2Cl_2$, the liquid phase is concentrated, the residue is combined with water, the mixture is extracted twice with ethyl acetate, and the combined ethyl acetate phases are washed with $NaHCO_3$ solution and water, dried and concentrated. 5.5 g (66% of theory) of N-(i-propyloxycarbonyl)-L-valine-diphenylmethylamide of a melting point of $145°$ C. are obtained.

The following compounds of the formula (I) are obtained analogously to Example 1

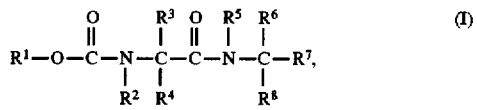

TABLE 1

| Example No. | $R^1$ | $R^2$ | $R^3$ | $R^4$ | $R^5$ | $R^6$ | $R^7$ | $R^8$ | Physical constants |
|---|---|---|---|---|---|---|---|---|---|
| 2 | $-CH(CH_3)_2$ | H | $-CH(CH_3)_2$ | H | H | H | phenyl | phenyl | m.p.: 164° C. |
| 3 | $s-C_4H_9$ | H | $-CH(CH_3)_2$ | H | H | H | phenyl | 4-Cl-phenyl | m.p.: 154° C. |
| 4 | $-CH(CH_3)_2$ | H | $-CH(CH_3)_2$ | H | H | H | 4-Cl-phenyl | 4-Cl-phenyl | m.p.: 184° C. |
| 5 | $s-C_4H_9$ | H | $-CH(CH_3)_2$ | H | H | H | 4-Cl-phenyl | 4-Cl-phenyl | m.p.: 167° C. |
| 6 | $-CH(CH_3)_2$ | H | $-CH(CH_3)_2$ | H | H | H | phenyl | 4-OCH$_3$-phenyl | m.p.: 162° C. |

TABLE 1-continued

| Example No. | R¹ | R² | R³ | R⁴ | R⁵ | R⁶ | R⁷ | R⁸ | Physical constants |
|---|---|---|---|---|---|---|---|---|---|
| 7 | s-C₄H₉ | H | —CH(CH₃)₂ | H | H | H | 4-OCH₃-C₆H₄— | C₆H₅— | m.p.: 115° C. |
| 8 | —CH(CH₃)₂ | H | —CH(CH₃)₂ | H | H | H | 4-F-C₆H₄— | 4-OCH₃-C₆H₄— | m.p.: 188° C. |
| 9 | s-C₄H₉ | H | —CH(CH₃)₂ | H | H | H | 4-F-C₆H₄— | 4-OCH₃-C₆H₄— | m.p.: 152° C. |
| 10 | C₆H₅— | H | —CH(CH₃)₂ | H | H | H | 4-F-C₆H₄— | 4-OCH₃-C₆H₄— | m.p.: 124° C. |
| 11 | cyclopentyl | H | —CH(CH₃)₂ | H | H | H | 4-OCH₃-C₆H₄— | 4-F-C₆H₄— | m.p.: 156° C. |
| 12 | —CH(CH₃)₂ | H | —CH(CH₃)₂ | H | H | H | 4-OCH₃-C₆H₄— | 4-F-C₆H₄— | m.p.: 160° C. |
| 13 | —CH(CH₃)₂ | H | —CH(CH₃)₂ | H | H | H | 4-OCH₃-C₆H₄— | 4-OCH₃-C₆H₄— | m.p.: 204° C. |
| 14 | s-C₄H₉ | H | —CH(CH₃)₂ | H | H | H | 4-OCH₃-C₆H₄— | 4-OCH₃-C₆H₄— | m.p.: 195° C. |
| 15 | C₆H₅— | H | —CH(CH₃)₂ | H | H | H | 4-OCH₃-C₆H₄— | 4-OCH₃-C₆H₄— | m.p.: 200° C. |
| 16 | cyclopentyl | H | —CH(CH₃)₂ | H | H | H | 4-OCH₃-C₆H₄— | 4-OCH₃-C₆H₄— | m.p.: 197° C. |
| 17 | —CH(CH₃)₂ | H | —CH₃—CH(C₂H₅)— | H | H | H | 4-OCH₃-C₆H₄— | 4-OCH₃-C₆H₄— | m.p.: 218° C. |

USE EXAMPLES:

In the use examples which follow, the compound given below was employed as comparison substance:

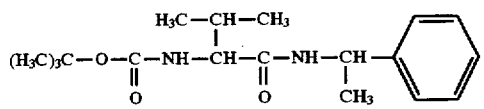
(A)

(disclosed in DE-OS (German Published Specification) 3,915,755)
N-(t-butyloxycarbonyl-L-valine-phenyl-ethylamide

Example A

Phytophthora Test (Tomato)/Protective
Solvent: 4.7 parts by weight of acetone
Emulsifier: 0.3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabin at 100% relative atmospheric humidity and approx. 20° C.

The evaluation takes place 3 days after the inoculation.

In this test, an effectiveness which is up to 100 degrees of effectiveness higher than the prior art is shown, for example, by the compounds of the following preparation examples: (1), (2) and (3), at an active compound concentration of 10 ppm.

Example B

Plasmopara Test (Grapevines)/Protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Plasmopara viticola* and then remain in a humidity cheer at 20° to 22° C. and 100% relative atmospheric humidity for 1 day. The plants are then placed in a greenhouse at 22° C. and about 80% atmospheric humidity for 5 days. The plants are then moistened and placed in a humidity chamber for 1 day.

Evaluation is carried out 7 days after the inoculation.

In this test, an effectiveness which is up to 100 degrees of effectiveness higher than the prior art is shown, for example, by the compounds of the following preparation examples: (1), (2) and (3), at an active compound concentration of 10 ppm.

We claim:

1. An amino acid amid derivative of the formula (I)

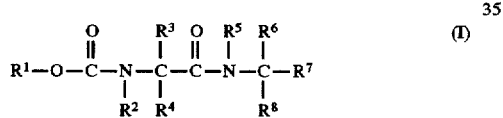

wherein $R^1$ represents methyl; ethyl; n- and i-propyl; n-, i-, s- and t-butyl; fluoromethyl; fluoroethyl; fluoropropyl; chloropropyl; fluorobutyl; chlorobutyl; difluoromethyl; difluoropropyl; dichloropropyl; difluorobutyl; dichlorobutyl; trifluoromethyl; trichloromethyl; trifluoroethyl; trichloroethyl; trifluoropropyl; trichloropropyl; trifluorobutyl; trichlorobutyl; allyl; butenyl; propargyl; butynyl; fluoro- or chloroallyl; fluoro- or chlorobutenyl; fluoro- or chloropropargyl; fluoro- or chlorobutynyl; cyclopropyl; cyclopentyl; cyclohexyl; cyclopentenyl; cyclohexenyl; phenyl; or phenyl monosubstituted to disubstituted by identical or different substitutents selected from the group consisting of methyl, ethyl, n- and i-propyl, n-, i-, s- and t-butyl, methoxy, ethoxy, i- and n-propoxy, n-, i-, s- and t-butoxy, trifluoromethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy, trifluoromethylthio, chlorine, bromine, and fluorine;

$R^2$ and $R^5$ represent hydrogen;

$R^3$ and $R^4$ are identical or different and represent hydrogen; methyl; ethyl; n- or i-propyl; n-, i-, s- or t-butyl; 3-pentyl; cyclopropyl; cyclopentyl; or cyclohexyl; or $R^3$ and $R^4$ together with the carbon atom to which they are bonded form a cyclopropyl, cyclopentyl, or cyclohexyl ring;

$R^6$ represents hydrogen; methyl; ethyl; n- and i-propyl; and $R^7$ and $R^8$ are identical or different and represent phenyl; pyridyl; furanyl; thienyl; or phenyl substituted by a substituent selected from the group consisting of methyl, ethyl, n- and i-propyl, n-, i-, s- and t-butyl, methoxy, ethoxy, i- and n-propoxy, n-, i-, s- and t-butoxy, trifluoromethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy, trifluoromethylthio, chlorine, bromine, fluorine, nitro, and cyano; or pyridyl, furanyl or thienyl substituted by a substituent selected from the group consisting of chlorine, fluorine, bromine and methyl;

with the exception of the compound [1-[[(diphenylmethyl)-amino]carbonyl]-2-methylpropyl]-1, 1-dimethylethylcarbamate.

* * * * *